US006969383B2

(12) United States Patent
Hildebrand

(10) Patent No.: US 6,969,383 B2
(45) Date of Patent: \*Nov. 29, 2005

(54) METHOD FOR TREATING SEVERE TINNITUS

(75) Inventor: Keith Robert Hildebrand, Houlton, WI (US)

(73) Assignee: Medtronic, Inc., Minneapolis, MN (US)

( * ) Notice: Subject to any disclaimer, the term of this patent is extended or adjusted under 35 U.S.C. 154(b) by 205 days.

This patent is subject to a terminal disclaimer.

(21) Appl. No.: 10/611,459

(22) Filed: Jul. 1, 2003

(65) Prior Publication Data

US 2004/0062819 A1 Apr. 1, 2004

Related U.S. Application Data

(63) Continuation-in-part of application No. 10/259,101, filed on Sep. 27, 2002, now Pat. No. 6,656,172.

(51) Int. Cl.[7] ............................ A61K 9/22; A61B 19/00
(52) U.S. Cl. .................................... 604/891.1; 128/898
(58) Field of Search ......................... 604/500, 28, 116, 604/891.1, 890.1, 151; 128/897–899

(56) References Cited

U.S. PATENT DOCUMENTS

| | | | | |
|---|---|---|---|---|
| 4,445,500 A | * | 5/1984 | Osterholm | 604/28 |
| 5,496,369 A | * | 3/1996 | Howard, III | |
| 5,676,655 A | * | 10/1997 | Howard, III et al. | |
| 5,711,316 A | * | 1/1998 | Elsberry et al. | 128/898 |
| 5,713,847 A | * | 2/1998 | Howard, III et al. | |
| 5,863,941 A | | 1/1999 | Liedtke | |
| 6,265,379 B1 | * | 7/2001 | Donovan | 514/14 |
| 6,309,410 B1 | * | 10/2001 | Kuzma et al. | 607/137 |
| 6,358,926 B2 | | 3/2002 | Donovan | |
| 6,656,172 B1 | * | 12/2003 | Hildebrand | 604/891.1 |
| 2002/0156512 A1 | * | 10/2002 | Borkan | 607/117 |

OTHER PUBLICATIONS

Kaneko, Megumi et al., Intrathecally Administered Gabapentin Inhibits Formalin–Evoked Nociception and the Expression of Fos–Like Immunoreactivity in the Spinal Cord of the Rat, J. Pharmacol Exp Ther, vol. 292, Issue 2, 743–751, Feb. 2000.*

Menkes, D B, et al.; "Sodium Valproate for Tinnitus"; Journal of Neurology Neurosurgery & Psychiarty, XX, XX, vol. 65, No. 5, (Nov. 1998) p. 803.

Simpson, J J, et al.; "A Review of Evidence in Support of a Role for 5–HT in the Perception of Tinnitus"; Hearing Research 2000 Netherlands, vol. 145, No. 1–2, 2000, pp. 1–7.

Uno, I. et al.; "A Rare Complication of Stellate Ganglion Block a Case Report"; Practica Otologica Kyoto; vol. 77, No. 12, 1984, pp. 2515–2519.

Gentili, Marc E.; "Epidural Fibrin Glue Injection Stops Postdural Puncture Headache in Patient With Long–Term Intrathecal Catheterization."; Regional Anesthesia and Pain Medicine, United States 2003; Jan.–Feb., vol. 28, No. 1; (Jan. 2003), p. 70.

Coffey, R J, et al.; "Abrupt Intrathecal Baciofen Withdrawal: Management of Potentially Life–Threatening Sequelae"; Neuromodulation 2001 United States, vol. 4, No. 4, 2001, pp. 142–146.

Lewis, J.E., S.D.G. Stephens, et al, "Tinnitus and suicide." Jul. 7, 1993, pp. 50–54, vol. 19, Clin Ototaryngol.

McFadden, D., Tinnitus: Facts, Theories, and Treatments, 1982, pp. 1–9, National Academy Press, Washington D.C.

(Continued)

*Primary Examiner*—Sharon Kennedy
(74) *Attorney, Agent, or Firm*—Banner, & Witcoff, Ltd.

(57) ABSTRACT

A method for treating severe tinnitus is disclosed. The method of the present invention comprises implanting a catheter into a patient and administering a drug formulation or fluid comprising a therapeutic agent intrathecally into the patient's cerebrospinal fluid.

55 Claims, 4 Drawing Sheets

OTHER PUBLICATIONS

Sataloff, J., R.T. Sataloff, et al., "Tinnitus and vertigo in healthy senior citizens without a history of noise exposure." Mar. 1987, pp. 87–89, vol. 2, Thieme Medical Publishers, Inc., New York, NY.

Axelsson, A. and A. Ringdahl, "Tinnitus–a study of its prevalence and characteristics.", 1989, pp. 53–56, vol. 23, British Journal of Audiology.

Coles, R. R. A., Thompson, et al., "Intra–tympanic injections in the treatment of tinnitus.", 1992, pp. 240–242, vol. 17, Clin Otolaryngol.

Dobie, R.A., "A review of randomized clinical trials in tinnitus.", The Laryngoscope, Aug. 1999, pp. 1202–1211, Lippincott Williams & Wilkins, Inc., Philadelphia.

Lockwood, A.H., R.J. Salvi, et al, "The functional neuroanatomy of tinnitus: Evidence for limbic system links and neural plasticity.", Jan., 1998, Neurology, pp. 114–120, vol. 50, American Academy of Neurology.

Moller, A.R., "Symptoms and signs caused by neural plasticity." Neurological Research, Sep., 2001, pp. 565–572, vol. 23, Forefront Publishing Group.

Den Hartigh, J., C. G. J. M. Hilders, et al., "Tinnitus suppression by Intravanous lidocaine in relation to its plasma concentration." Clinical Pharmacology & Therapeutics, Oct. 1993, pp. 415–420, vol. 54 No. 4, Mosby–Year Book, Inc.

Ochi, K. and J.J. Eggermont, "Effects of salicylate on neural activity in cat primary auditory cortex." Hearing Research, 1996, pp. 63–76, vol. 95, Elsevier Science B.V.

Caspary, D.M., J. C.Milbrandt, et al., "Central Auditory Aging: GABA Changes in the Inferior Colliculus."Experimental Gerontology, 1995, pp. 349–360, vol. 30 Nos. 3/4, Elsevier Science Ltd., USA.

McGeer, E. G. and P. L. McGeer, "Age Changes in the Human for Some Enzymes Associated with Metabolism of the Catecholamines, GABA and Acetycholine." Neurobiology of Aging, 1975, pp. 287–305, Plenum Press, New York.

Raza, A., J. C. Milbrandt, et al., "Age–Related Changes in Brainstem Auditory Neurotransmitters: Measures of GABA and Acetylcholine Function." Hearing Research, 1994, pp. 221–230, vol. 77, Elsevier Science B. V.

Araki, T., H. Kato, et al., "Selective changes of neurotransmitter receptors in middle–aged gerbil brain." Neurochem. Int., 1993, pp. 541–548, vol. 23 No. 6, Pergamon Press Ltd.

Mildbrandt, J. C., R. L. Albin, et al., "Age–Related Decrease in $GABA_a$ Receptor Binding in the Fischer 344 Rat Inferior Colliculus." Neurobiology of Aging, 1994, pp. 699–703, vol. 15 No. 6, Elsevier Science Ltd., USA.

Moller, A. R., M. B. Moller, et al., "Some Forms of Tinnitus May Involve the Extralemniscal Auditory Pathway." Laryngoscope, Oct 1992, pp. 1165–1171.

Szczrpaniak, W. S. and A. R. Moller, "Effects of L–Baclofen and D–Bachlofen on the Auditory System: A Study of Click–Evoked Potentials From the Inferior Colliculus in the Rat." Ann Otol Rhinol Laryngol, 1995, pp. 399–404.

Szczrpaniak, W. S. and A. R. Moller, "Effects of (–) baclofen, clonazepam, and diazepam on tone exposure–induced hyperexcitability of the inferior colliculus in the rat: possible therapeutic implications for pharmacological management of tinnitus and hyperacusis." Hearing Research, 1996, pp. 46–53, Elsevier Science B.V.

Lees, A. J., C. R. Clarke et al., "Hallucinations After Withdrawal of Baclofen." The Lancet, Apr. 16, 1977.

Zapp, J. J., "Gabapentin for the treatment of tinnitus: A case report." ENT–Ear, Nose & Throat Journal, Feb. 2001, pp. 114–116.

Kuzniecky, R. S. Ho, et al., "Modulation of cerebral GABA by topiramate, lamotrigine, and gabapentin in healthy adults." Neurology, Feb. 2002, pp. 368–372, AAN Enterprises, Inc.

Petroff, O. A., F. Hyder, et al., "Effects of Gabapentin on Brain GABA, Homocamosine, and Pyrrolidinone in Epilepsy Patients." Epilepsia, 2000, pp. 675–680, Lippincott Williams & Wilkins, Inc., Baltimore.

Westerberg, B. D., J. B. Roberson, et al., "A double–blind placebo–controlled trial of baclofen in the treatment of tinnitus." The American Journal of Otology, 1996, pp. 896–903, The American Journal of Otology, Inc.

Coffey, R. J., D. Cahill, et al., "Intrathecal baclofen for intractable spasticity of spinal origin: results of a long–term multicenter study." J Neurosurg, Feb. 1993, pp. 226–232, vol. 78.

Meythaler, J. M., S. Guin–Renfroe, et al., "Continuously Infused Intrathecal Baclofen for Spastic/Dystonic Hempiplegia." American Journal of Physical Medicine & Rehabilitation, 1999, pp. 155–161, No. 9, Lippincott Williams & Wilkins, Inc.

Penn, R. D., S. M. Savoy, et al., "Intrathecal Baclofen for Severe Spinal Spasticity." New England Journal of Medicine, Jun. 8, 1989, pp. 1571–1521, vol. 320.

Knutsson, E., U. Lindblom, et al., "Plasma and Cerebrospinal Fluid Levels of Baclofen (Lioresal®) at Optimal Therapeutic Responses in Spastic Paresis." Journal of the neurological Sciences, 1974, pp. 473–484, vol. 23, Elsevier Scientific Publishing Company, Netherlands.

Kroin, J. S., "Intrathecal Drug Administration." Clin. Pharmacokinet. 1992, pp. 319–326, vol. 22 (5), Adis International Limited.

Kroin, J. S. and R.D. Penn, "Cerebrospinal fluid pharmacokinetics of lumbar intrathecal baclofen", 1991, pp. 67–77, Parthenon Publishing.

Muller, H., J. Zierski, et al. "Pharmacokinetics of Intrathecal Baclofen." 1998, pp. 223–226, Springer–Verlag.

MilBrandt, JC, et al., "GAD levels and muscimol binding in rat inferior colliculus following acoustic trauma." Hearing Research, 2000, pp. 251–260, vol. 147 (1–2), Elsevier Science B.V.

Caspary, D.M., T.M. Holder, et al., "Age–Related Changes in $GABA_A$ Receptor Subunit Composition and Function in Rat Auditory System." Neuroscience, 1999, pp. 307–312, vol. 93, Elsevier Science, Ltd.

Milbrandt JC, Hunter C, et al., "Alterations of $GABA_A$ Receptor Subunit mRNA Levels in the Aging Fischer 344 Rat Inferior Colliculus." The Journal of Comparative Neurology, 1997, pp. 455–465, vol. 379, Wiley–Liss, Inc.

Milbrandt JC, et al., "$GABA_A$ Receptor Binding in the Aging Rat Inferior Colliculus." Neuroscience, 1996, pp. 449–458, vol. 73, No. 2, Elsevier Science Ltd., Great Britain.

Simpson, J. J. et al. "Recent advances in the pharmacological treatment of tinnitus." Trends is Pharmacology Sciences, Jan. 1999, vol. 20.

Jastreboff, P., et al., "Neurophysiological approach to tinnitus patients." The American Journal of Otology, 1996, pp. 236–240, vol. 17, The American Journal of Otology, Inc.

Merchant, S.N. et al., "Vestibular effects of Intravenous lidocaine used in the treatment of tinnitus." The Journal of Laryngology and Otology, Nov. 1986, pp. 1249–1253, vol. 100.

Podoshin, L., M. et al., "Treatment of tinnitus by intratympanic installation of lignocaine (lidocaine) 2 per cent through ventilation tubes." The Journal of Laryngology and Otology, Jul. 1992, pp. 603–606, vol. 106.

Raza, A., et al., "Age–related changes in brainstem auditory neurotransmitters: measures of GABA and acetylcholine function." Hearing Research, 1994, pp. 221–230, vol. 77, Elsevier Science B.V.

Kaltenbach, J. A. "Neurophysiologic Mechanisms of Tinnitus." Journal of the American Academy of Audiology, Mar. 2000, pp. 125–137, vol. 11, No. 3.

* cited by examiner

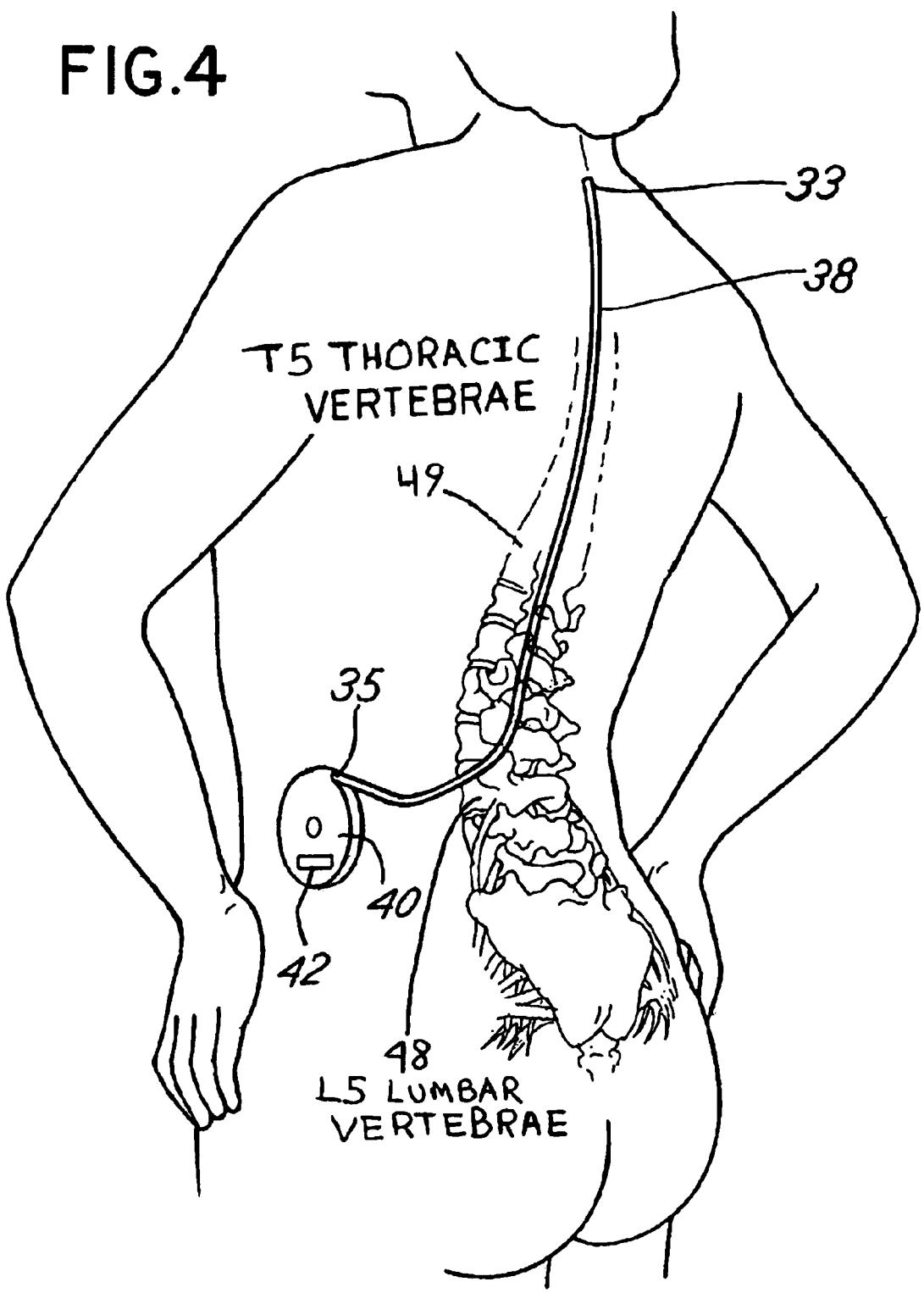

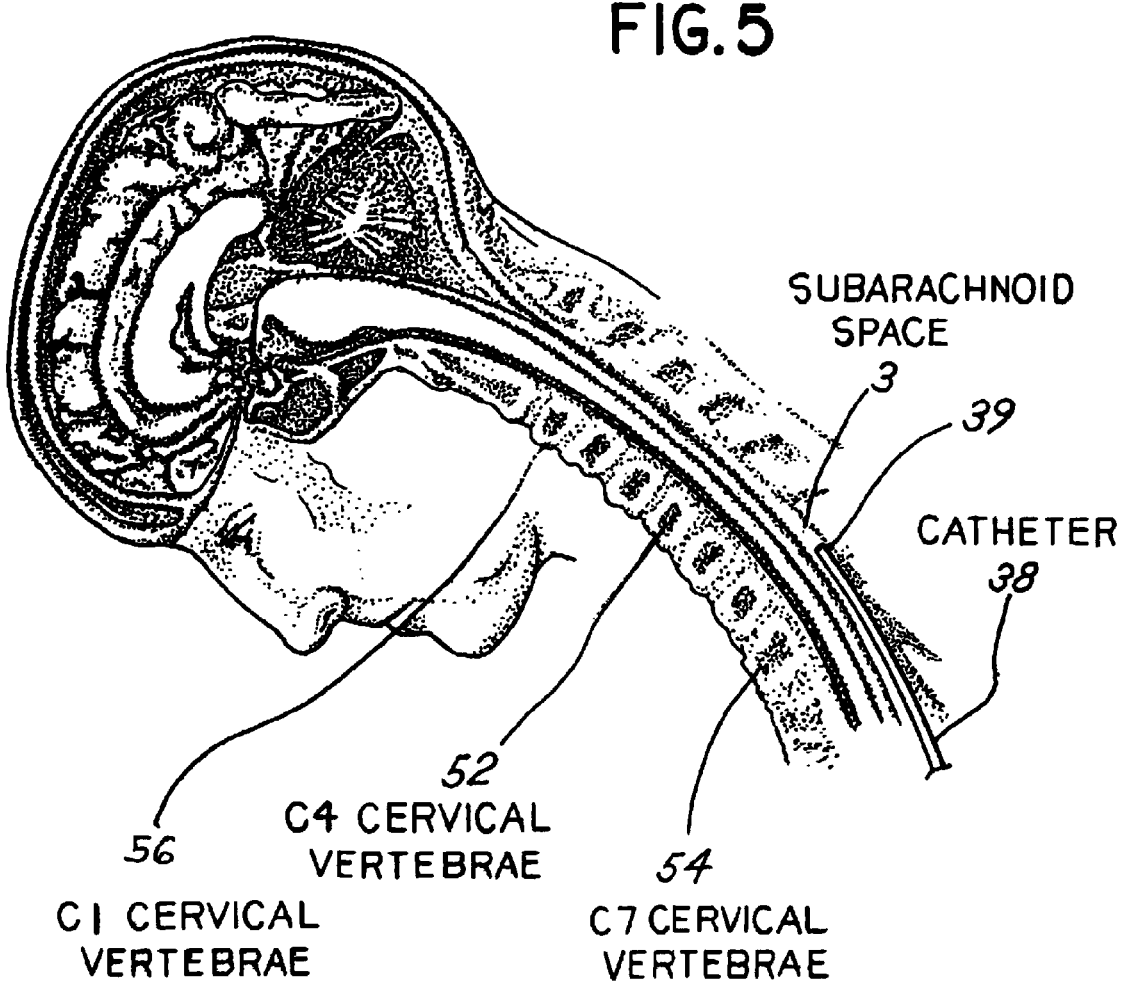

METHOD FOR TREATING SEVERE TINNITUS

This is a continuation-in-part of application Ser. No. 10/259,101, filed Sep. 27, 2002, now U.S. Pat. No. 6,656,172, for which priority is claimed. This parent application is incorporated herein by reference in its entirety.

FIELD OF THE INVENTION

This invention relates to a method for treating severe tinnitus.

BACKGROUND OF THE INVENTION

Tinnitus is the perception of ringing, hissing, or other sounds in the ears or head when no external sound is present. For some people, tinnitus is just a nuisance. For others, it is a life-altering condition. According to the American Tinnitus Association, over 50 million Americans experience tinnitus to some degree and of these, approximately 12 million people have tinnitus to a distressing degree.

Approximately 2 million Americans have tinnitus to the point where they are so seriously debilitated that they cannot function on a "normal" day-to-day basis and some may commit suicide. Lewis, J. E., S. D. G. Stephens, et al. (1993). "Tinnitus and suicide." *Clin Otolaryngol* 19: 50–54. It is this severely affected population, which is only poorly managed with therapies available today, that may benefit from intrathecal pharmacotherapy proposed in the current investigation.

In terms of population percentages, approximately 17% of the general population, and 33% of the elderly population suffer from tinnitus. McFadden, D. (1982). *Tinnitus: Facts, Theories, and Treatments*. Washington D.C., National Academy Press; and Sataloff, J., R. T. Sataloff, et al. (1987). "Tinnitus and vertigo in healthy senior citizens without a history of noise exposure." *Am J Otol* 8(2): 87–89.

Axelsson and Ringdahl reported that approximately 2.5% of the tinnitus patients that they surveyed complained that tinnitus "plagued me all day." Axelsson, A. and A. Ringdahl (1989). "Tinnitus-a study of its prevalence and characteristics." *British Journal of Audiology* 23: 53–62. In Western countries various investigators have reported 0.5% to 1.0% of the population are severely affected by tinnitus to the extent that it interferes with their normal working and leisure life. Coles, R. R. A., A. C. Thompson, et al. (1992). "Intra-tympanic injections in the treatment of tinnitus." *Clin Otolaryngol* 17(3): 240–242.

Despite the large medical impact of tinnitus, no widely accepted, effective treatment exists for the majority of cases of tinnitus. Dobie, R. A. (1999). "A review of randomized clinical trials in tinnitus." *The Laryngoscope* 109: 1202–1211; Simpson, J. J. and W. E. Davies (1999). "Recent advances in the pharmacological treatment of tinnitus." *TiPS* 20: 12–18.

In the vast majority of tinnitus cases an underlying cause is not apparent, and effective treatments (i.e., treatments which actually eliminate or reduce the sound) are not available. Most of the therapies that are presently available attempt to minimize the patients' awareness of the tinnitus symptoms or reduce their emotional reaction to their condition.

Rational treatment for the small proportion of patients with a reversible cause for their tinnitus involves correcting the underlying condition. This may involve removing or reducing the dose of the pharmacologic mediator (e.g., aspirin, aminoglycoside) or correcting the mechanical defect in the peripheral auditory system (e.g., remove obstructions in external auditory canal, surgically correct middle ear problems, or surgically decompress microvascular compressions of the auditory nerve).

Audiological Management

The most common method used to manage mild to moderate tinnitus is masking. In its simplest form, masking consists of self-exposure to background noise such as, radio, television, or recorded music. People with normal hearing and severe tinnitus can wear a small hearing-aid-like device that produces background (masking) noise in the affected ear. Patients with concomitant impaired hearing and tinnitus sometimes benefit (both their hearing and tinnitus) from use of a conventional hearing aid.

Psychotherapy

Limbic structures of the brain may be involved in the neural plastic changes associated with tinnitus. Supportive of this notion is the observation that the perceived amplitude of the tinnitus often does not correspond to the overall severity of the condition. For example, some patients with tinnitus of a relatively low volume are extremely disturbed, whereas others with high volume tinnitus are relatively unaffected by it. Lockwood, A. H., R. J. Salvi, et al. (1998). "The functional anatomy of gaze-evoked tinnitus: Evidence for limbic system links and neural plasticity." *Neurology* 50: 114–120.

Some researchers have used this observation to justify treatments based upon a habituation counseling strategy. Jastreboff, P. J., W. C. Gray, et al. (1996). "Neurophysiological approach to tinnitus patients." *Amer J Otol* 17: 236–240. Habituation is a psychological technique that trains patients to ignore or minimize their emotional reaction to tinnitus. Habituation is traditionally defined as the disappearance of reactions to sensory stimuli because of repetitive exposure and the lack of positive or negative reinforcement. A necessary condition for inducing habituation is to remove the association between tinnitus and the emotional state, i.e., to remove the activation of the limbic system by the tinnitus signal. The most popular version of this therapy, tinnitus retraining therapy, has been developed and popularized by Dr. Pawel Jastreboff. The process typically requires approximately 12 months of therapy. Treatments tend to be more successful for mild and moderate forms of tinnitus and for cases of shorter duration.

Psychoactive Drugs

The drugs most commonly used to manage tinnitus are antidepressants (especially tricyclics) and anxiolytics (valium, alprazolam, buspirone), although they have limited efficacy. Anxiolytics and antidepressants affect the secondary psychological sequelae of tinnitus, rather than the perception of the noise itself. The neural plasticity associated with tinnitus may involve the formation of new neural connections between the auditory and limbic systems of the brain. Moller, A. R. (2001). "Symptoms and signs caused by neural plasticity." *Neurological Research* 23: 565–572.

Although numerous other drugs have been tried, the majority of clinical trials have produced negative results. Dobie, R. A. (1999). "A review of randomized clinical trials in tinnitus." *The Laryngoscope* 109: 1202–1211. Most agents have been administered orally, although several clinical trials attempting to directly administer agents into the ear have also failed to show efficacy. Coles, R. R. A., A. C. Thompson, et al. (1992). "Intra-tympanic injections in the treatment of tinnitus." *Clin Otolaryngol* 17(3): 240–242.

Pharmacologic Tinnitolytic Agents

Lidocaine

Intravenously (IV) administered lidocaine is the only drug that has demonstrated consistent, significant, and reproducible efficacy against tinnitus. den Hartigh, J., C. G. J. M. Hilders, et al. (1993). "Tinnitus suppression by intravenous lidocaine in relation to its plasma concentration." Clin Pharmaocol & Ther 54: 415–420. Unlike other commonly prescribed oral medications that tend to manage only the emotional symptoms associated with tinnitus, lidocaine actually reduces or eliminates the noise. Lidocaine ameliorates tinnitus in approximately 60–80% of sufferers, a result that has been replicated in numerous well-controlled clinical trials. Merchant, S. N. and M. V. Kirtane (1986). "Vestibular effects of intravenous lidocaine used in the treatment of tinnitus." J Laryngol Otol 100: 1249–1253. The efficacy of IV lidocaine is greater than the efficacy produced by auditory nerve transection (approximately 50%), suggestive of a central mechanism of lidocaine action. However, locally administered lidocaine (to the ear or cochlea) has been relatively ineffective. In addition, locally administered lidocaine to the ear has been associated with significant vestibular side effects such as vertigo and nausea. Ochi, K. and J. J. Eggermont (1996). "Effects of salicylate on neural activity in cat primary auditory cortex." Hearing Research 95(1–2): 63–76; Podoshin, L., M. Fradis, et al. (1992). "Treatment of tinnitus by intratympanic installation of lignocaine (lidocaine) 2 per cent through ventilation tubes." J Laryngol Otol 106(7): 603–606.

Despite the efficacy of IV lidocaine, it unfortunately does not represent a clinically useful therapy. Tinnitus patients effectively treated with IV lidocaine in the short term, usually experience a return of their symptoms shortly after the medication has been stopped. Intravenous lidocaine (bolus administration) has a short duration of action (10–20 minutes) and is metabolized rapidly by the liver (terminal half life of 1.5 to 2 hours in humans). Lidocaine used in the treatment of cardiac arrhythmias is typically diluted with saline, and administered as a precisely-metered IV infusion. Unfortunately in tinnitus patients with healthy heart rhythms, IV lidocaine can induce potentially life-threatening cardiac arrhythmias. Intravenous lidocaine at effective doses also can cause nausea and dizziness. If administered orally, lidocaine is ineffective due to a major first pass effect.

Baclofen

Tinnitus is associated with abnormal spontaneous neural activity at multiple levels within the central auditory pathways. Gamma-amino-butyric acid (GABA) is the main inhibitory neurotransmitter of the mammalian CNS. An example of a $GABA_B$-receptor agonist is baclofen, which mimics in part the effects of GABA.

Several studies have correlated age-related changes in the concentrations of GABA and $GABA_B$-binding sites in the Inferior Colliculus ("IC"), the major auditory midbrain structure. Caspary, D. M., J. C. Milbrandt, et al. (1995). "Central auditory aging: GABA changes in the inferior colliculus." Experimental Gerontology 30(3/4): 349–360; Raza, A., J. C. Milbrandt, et al. (1994). "Age-related changes in brainstem auditory neurotransmitters: measures of GABA and acetylcholine function." Hear Res 77(1–2): 221–230. Age-related decreases in the enzyme responsible for GABA synthesis (glutamic acid decarboxylase) have been reported in the IC of both rats and humans. McGeer, E. G. and P. L. McGeer (1975). Age changes in the human for some enzymes associated with metabolism of the catecholamines, GABA and acetycholine. Neurobioloby of Aging. J. Ordy, Brizzee K R. New York, Plenum Press: 287–305; Raza, A., J. C. Milbrandt, et al. (1994). "Age-related changes in brainstem auditory neurotransmitters: measures of GABA and acetylcholine function." Hear Res 77(1–2): 221–230. In rats, age-related decreases in the levels of GABA and the number of $GABA_B$-binding sites within the IC have also been reported. Araki, T., H. Kato, et al. (1993). "Selective changes of neurotransmitter receptors in middle-aged gerbil brain." Neurochem Int 23(6): 541–548; Milbrandt, J. C., R. L. Albin, et al. (1994). "Age-related decrease in GABAB receptor binding in the fischer 344 rat inferior colliculus." Neurobiol Aging 15(6): 699–703. These biochemical findings may explain why tinnitus is more prevalent among the elderly.

In addition to age-related biochemical changes, the inferior colliculus also shows changes in function (increased spontaneous activity) in response to noise exposure or injury to the peripheral auditory system, results commonly associated with tinnitus in humans. Moller, A. R., M. B. Moller, et al. (1992). "Some forms of tinnitus may involve the extralemniscal auditory pathway." Laryngoscope 102(10): 1165–1171. In rats, IV baclofen inhibited noise-induced electrical potentials recorded directly from IC neurons. Szcepaniak, W. S. and A. R. Moller (1995). "Effects L-baclofen and D-baclofen on the auditory system: a study of click-evoked potentials from the inferior colliculus in the rat." Ann Otol Rhinol Laryngol 104(5): 399–404; Szcepaniak, W. S. and A. R. Moller (1996). "Effects of (–) baclofen, clonazepam, and diazepam on tone exposure-induced hyperexcitability of the inferior colliculus in the rat: Possible therapeutic implications for pharmacological management of tinnitus and hyperacusis." Hear Res 97: 46–53. An additional observation suggestive of the inhibitory role of GABA in the normal auditory system comes from clinical reports of auditory hallucinations that are sometimes experienced with baclofen withdrawal in humans. Lees, A. J., C. R. Clarke, et al. (1977). "Hallucinations after withdrawal of baclofen." Lancet 8016: 858.

Additional evidence that may implicate GABA in the pathophysiology of tinnitus are: 1) Benzodiazepines are often used with moderate efficacy to treat tinnitus. As sedatives, they may reduce the stress associated with tinnitus. However, benzodiazepine-mediated modulation of GABAA receptors may also be involved. 2) Anecdotal reports describe the efficacy of gabapentin in tinnitus patients. Zapp, J. J. (2001). "Gabapentin for the treatment of tinnitus: A case report." ENT-Ear, Nose & Throat Journal: 114–116. Although the precise molecular mechanisms of gabapentin remain elusive, it is generally believed that gabapentin augments central GABA functions either by promoting its release and/or inhibiting its degradation. Kuzniecky, R., S. Ho, et al. (2002). "Modulation of cerebral GABA by topiramate, lamotrigine, and gabapentin in healthy adults." Neurology 58: 368–372; Petroff, O. A., F. Hyder, et al. (2000). "Effects of gabapentin on brain GABA, homocarnosine, and pyrrolidinone in epilepsy patients." Epilepsia 41(6): 675–680.

In light of the above preclinical data, a single placebo controlled human clinical trial was conducted to evaluate the efficacy of oral baclofen ($\leq 60$ mg/day) to treat tinnitus. Westerberg, B. D., J. B. Roberson, et al. (1996). "A double-blind placebo-controlled trial of baclofen in the treatment of tinnitus." Am J Otolaryngol 17: 896–903. The authors conducted a randomized, double-blinded study after anecdotal reports described patients who experienced beneficial subjective reduction in tinnitus while taking oral baclofen. The clinical trial used oral baclofen, up to 60 mg/day, in patients with chronic tinnitus. Not all of the patients had severe tinnitus, and for some, tinnitus was not their primary complaint. After a 3-week course of escalating doses (20 mg/day×1 week; then 40 mg/day×1 week; then 60 mg/day×1 week) subjects were retested using the Tinnitus Handicap Inventory, loudness and pitch matching, and maskability of tinnitus using white noise. Subjective improvement in tinnitus occurred in only 9.7% of baclofen-treated patients as opposed to 3.4% in placebo-treated patients. This outcome was not statistically significant. Oral baclofen therapy was associated with significant side effects that included sedation, confusion, dizziness, GI upset, and weakness, the combination of which caused 25% of the enrolled patients to drop out of the trial.

These side effects are also associated with oral baclofen used to treat spasticity but are typically not a problem when baclofen is administered intrathecally to treat spasiticity. Coffey, R. J., D. Cahill, et al. (1993). "Intrathecal baclofen for intractable spasticity of spinal origin: results of a long-term multcenter study." *J Neurosurg* 78: 226–232; Meythaler, J. M., S. Guin-Renfroe, et al. (2001). "Continuously infused intrathecal baclofen over 12 months for spastic hypertonia in adolescents and adults with cerebral palsy." *Arch Phys Med Rehabil* 82: 155–161; Penn, R. D., S. M. Savoy, et al. (1989). "Intrathecal baclofen for severe spinal spasticity." *New England Journal of Medicine* 320: 1571–1521.

Benzodiazepines

Another type of $GABA_A$ agonist are the general class of molecules known as benzodiazepines. By acting at $GABA_A$ receptors, benzodiazepines act to inhibit neuronal activity and have proven to be useful in decreasing neuronal hyperactivity associated with epilepsy and anxiety.

Benzodiazepines are also commonly used in anesthesiology as tranquilizers. In addition to quelling the hyperactive neurons associated with tinnitus, these agents may offer the added benefit of decreasing anxiety, a common comorbidity associated with severe tinnitus. Two drugs in the benzodiazepine family are midazolam and alprazolam, both of which may be useful in the management of tinnitus.

Gabapentin

Gabapentin is a GABA-agonist-like drug. Because it does not bind directly to GABA receptors, it is not a true pharmacologic GABA agonist. On the other hand, it is known that gabapentin produces inhibitory effects like GABA on selective neuronal populations and thus has been useful in treating several diseases characterized by hyperactivity of central neurons including epilepsy and neuropathic pain. Since the pathophysiology of chronic severe tinnitus appears to be similar to neuropathic pain (plastic neural changes leading to central facilitation of synaptic transmission), many drugs that are effective for neuropathic pain may be effective for tinnitus. Indeed, reports both in animal models and humans suggest that oral gabapentin may be useful in reducing tinnitus. "Gabapentin for the treatment of tinnitus: a case report." Zapp, J J., *Ear Nose Throat J.*, 80(2): 114–116 (February 2001); "Assessing tinnitus and prospective tinnitus therapeutics using a psychophysical animal model." Bauer, C A and Brozoski, T J.,*J. Assoc. Res. Otolaryngol.*, 2(1): 54–64 (March 2001). Because gabapentin does not readily penetrate the blood-brain barrier, intrathecal delivery should produce higher more effective concentrations of gabapentin in the CNS.

Thyrotropin-releasing hormone (TRH)

TRH, a peptide neurotransmitter in the CNS, has been suggested as a useful agent for treating both mood disorders and epilepsy by acting primarily to inhibit the activity of glutamine-containing neurons. Glutamine is the major excitatory neurotransmitter of the CNS and may be associated with increased activity of the central auditory neurons involved in tinnitus. The loss of GABA-containing neurons with aging, results in an increased activity of glutamine-containing neurons that may be controlled by supplying exogenous TRH.

Sodium Valproate

Sodium valproate is another agent that is used to treat central diseases of the nervous system associated with increased neuronal activity. Clinically it is used to treat both epilepsy and as a mood stabilizer to treat bipolar disorder. Although the exact mechanisms of action of valproate are unknown, it may enhance the accumulation of GABA within the CNS and thus may be useful in decreasing central hyperactive neurons associated with tinnitus.

U.S. Pat. No. 5,676,655 discloses a method for implanting a neural prosthetic drug delivery apparatus into a target zone of a patient's brain for reducing or eliminating the effects of tinnitus. The apparatus includes a catheter that is inserted into the patient's auditory cortex or thalamus. The catheter microinfuses drugs that suppress or eliminate abnormal neural activity into geometrically separate locations of the patient's cortex or thalamus, thereby reducing or eliminating the effects of tinnitus. The patent, however, deals with drug delivery directly into brain tissue or into specific anatomical structures, i.e. intraparenchymal drug delivery. There are a number of disadvantages to intraparenchymal drug delivery to treat severe tinnitus. For example, intraparenchymal drug delivery is relatively invasive and requires a highly trained neurosurgeon to implant the catheter into the brain tissue or specific anatomical structure.

SUMMARY OF THE INVENTION

One or more of the above-mentioned deficiencies in the art are satisfied by the method of the present invention of intrathecal drug delivery for the treatment of severe tinnitus. One embodiment of the invention involves the use of a drug formulation infused intrathecally to treat tinnitus. For example, a catheter is implanted into a patient, the catheter having a proximal end and a distal end. The distal end of the catheter is adapted to infuse the drug formulation intrathecally into a patient's cerebrospinal fluid. The drug formulation may comprise a solvent and at least one therapeutic agent such as baclofen, gabapentin, sodium valproate, a benzodiazepine such as midazolam or alprazolam, or a thyrotropin-releasing hormone.

In one embodiment of the invention, the proximal end of the catheter is coupled to an implantable pump and the distal end of the catheter is inserted into the subarachnoid space of a patient's spinal column. The implantable pump is operated to deliver a fluid that may comprise a therapeutic agent such as gabapentin, sodium valproate, or a thyrotropin-releasing hormone. The fluid is pumped through the distal end of the catheter and directly into the cerebrospinal fluid contained in the subarachnoid space of the patient's spinal column.

These and other advantages and features of the invention will become apparent upon reading and following the detailed description and referring to the accompanying drawings which like numbers refer to like parts throughout.

BRIEF DESCRIPTION OF THE DRAWINGS

FIG. 4 is a diagrammatic illustration of an implanted catheter and pump in accordance with an embodiment of the present invention.

FIG. 5 is a diagrammatic illustration of a catheter implanted in a patient's subarachnoid space for the delivery of a therapeutic agent or agents into the cerebrospinal fluid.

DETAILED DESCRIPTION OF THE PREFERRED EMBODIMENTS

Figure 1:
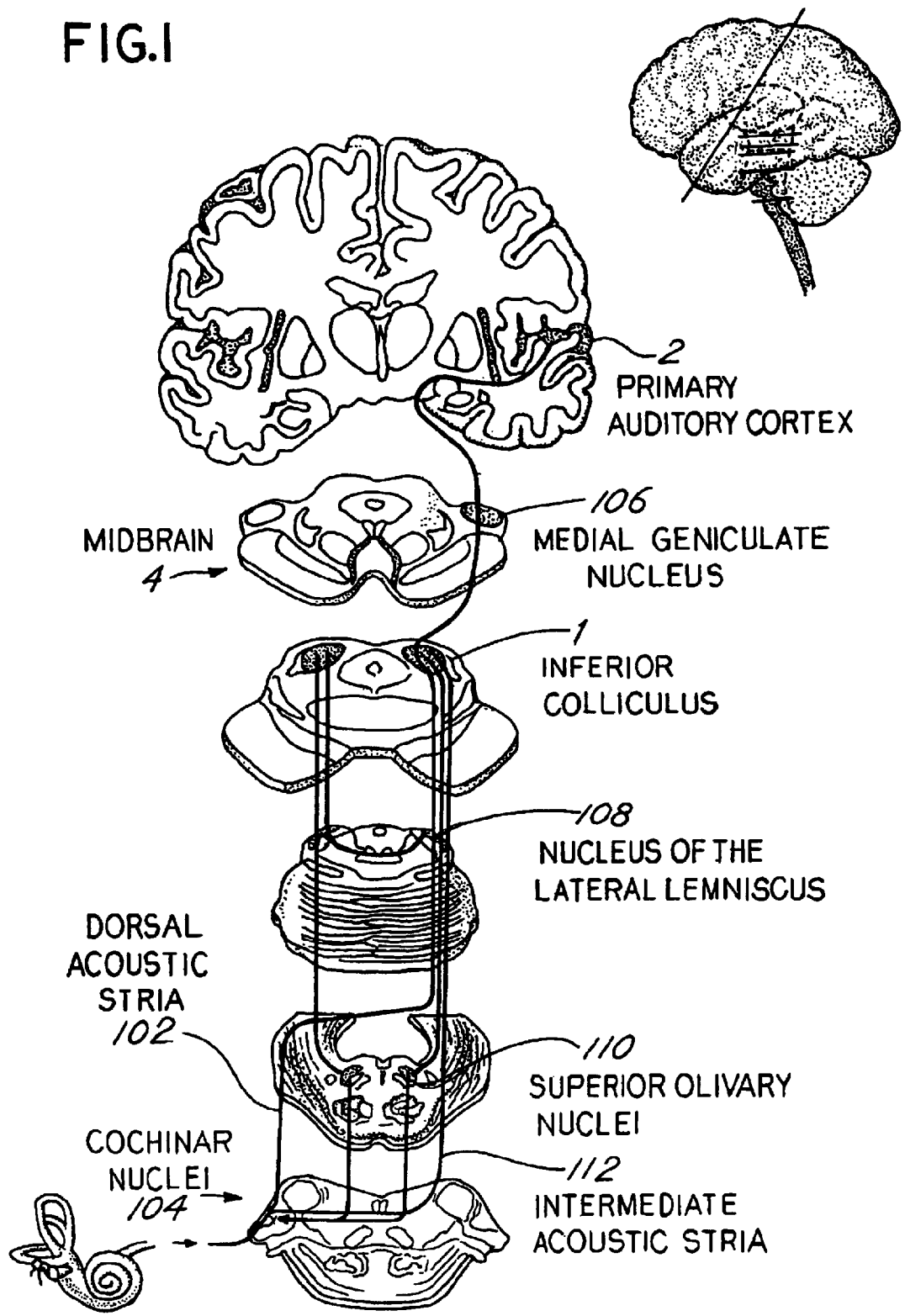
FIG. 1 is a diagrammatic illustration of the central auditory pathways.
Figure 2:
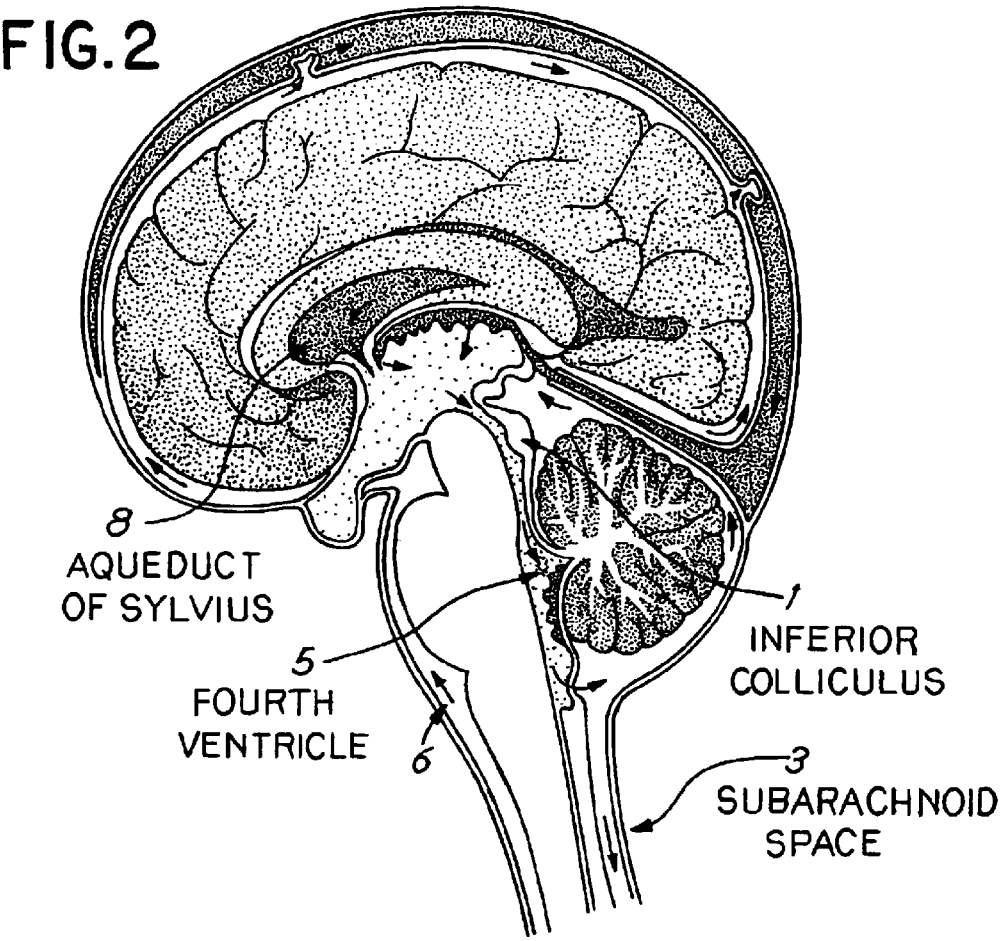
FIG. 2 is a diagrammatic illustration of the location of a patient's inferior colliculus and the flow of cerebrospinal fluid in the subarachnoid space.

As illustrated in FIG. 1, the central auditory pathways comprise, the inferior colliculus 1, the auditory cortex 2, the dorsal acoustic stria 102, the cochlear nuclei 104, the geniculate nucleus 106, the nucleus of the lateral lemniscus 108, the superior olivary nuclei 110, and the intermediate acoustic stria 112. Experimental evidence suggests that the dorsal cochlear nuclei 104, the inferior colliculus 1, and the auditory cortex 2, as shown in FIGS. 1 and 2, may be involved in the generation of tinnitus. Kaltenbach, J. A. (2000). "Neurophysiologic mechanisms of tinnitus." *J Am Acad Audiol* 11: 125–137. These major auditory structures are relatively shallow brain structures that lie in close proximity to the subarachnoid space 3 as shown in FIG. 2.

The inferior colliculus 1 lies on the dorsal surface of the midbrain 4 and rostral (cephalad) to the fourth ventricle 5 and dorsal to the cerebral aqueduct of Sylvius 8. The superficial surface of the inferior colliculus 1 is bathed in cerebrospinal fluid (CSF) 6 that exits the foramina of Magendie and Luschka to flow around the brainstem and cerebellum. The arrows within the subarachnoid space 3 in FIG. 2 indicate cerebrospinal fluid 6 flow.

The subarachnoid space 3 is a compartment within the central nervous system that contains cerebrospinal fluid 6. The cerebrospinal fluid 6 is produced in the ventricular system of the brain and communicates freely with the subarachnoid space 3 via the foramina of Magendie and Luschka.

As previously discussed in the background of the invention, available evidence suggests that tinnitus arises within the central auditory structures of the brain, and that those structures represent an important target for therapeutic agents. Given the limited efficacy of other treatments, intrathecal delivery of therapeutics into the cerebrospinal fluid 6 in accordance with the present invention offers the potential to reduce the perception of tinnitus in a large portion of severely affected patients who currently have very limited options.

The therapeutic agent or agents may include baclofen, gabapentin, sodium valproate, a benzodiazepine such as midazolam or alprazolam, or a thyrotropin-releasing hormone. Each of the agents may be combined with a solvent to form a drug formulation that may be administered intrathecally to a patient. The solvent may comprise sterile water or a 0.9% saline solution. In addition, the drug formulation may comprise an effective amount of NaCl to make the drug formulation isotonic. The drug formulation may have a pH between 4 and 9 and more preferably a pH between 5 and 7. Also, the drug formulation may be substantially free of preservatives and may contain cyclodextrin acting as an excipient to increase solubility.

Intrathecal delivery of therapeutics into the cerebrospinal fluid is less invasive than intraparenchymal (direct tissue) delivery of therapeutics. In addition, intrathecal delivery of therapeutics may not require the need for a neurosurgeon as the delivery of the therapeutics does not require delivery to a direct brain target. Numerous other physicians may be qualified to insert a catheter into the lumbar subarachnoid space of the spinal column in order to initiate intrathecal therapeutic delivery.

Figure 3:
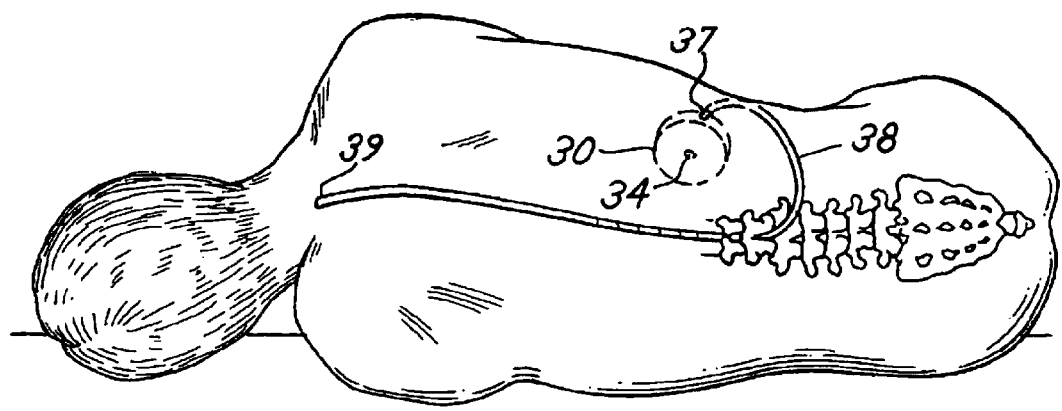
FIG. 3 is diagrammatic illustration of a catheter implanted in a patient according to an embodiment of the present invention.

Referring to FIG. 3, a system or device 30 may be implanted below the skin of a patient. The device 30 has a port 34 into which a hypodermic needle can be inserted through the skin to inject a quantity of therapeutic agent. The therapeutic agent is delivered from device 30 through a catheter port 37 into a catheter 38. Catheter 38 is positioned so that the distal tip 39 of catheter 38 is positioned in the subarachnoid space 3 between the fourth cervical vertebrae (C4) 52 and the seventh cervical vertebrae (C7) 54, as shown in FIG. 5. The distal tip 39 can be placed in a multitude of locations to deliver a therapeutic agent into the cerebrospinal fluid of the patient. In one embodiment, the distal tip 39 of catheter 38 is inserted in the subarachnoid space 3 between the fourth cervical vertebrae (C4) 52, and the seventh cervical vertebrae (C7) 54, to allow for relatively high therapeutic dose infusion concentrations in the intracranial CSF compartment near the inferior colliculus 1 while minimizing spinal exposure. In other embodiments, the distal tip 39 of the catheter 38 is inserted in the subarachnoid space 3 between the fifth thoracic (T5) 49 (FIG. 4) and the first cervical vertebrae (C1) 56, or in the subarachnoid space 3 between the fifth lumbar (L5) 48 (FIG. 4) and fifth thoracic vertebrae (T5) 49 (FIG. 4). While device 30 is shown in FIG. 3, delivery of a therapeutic agent into the CSF to treat severe tinnitus can be accomplished by simply injecting the therapeutic agent via port 34 to catheter 38.

A higher concentration of baclofen delivered intrathecally into the CSF in accordance with the present invention can provide improved reduction of the perception of tinnitus in a large proportion of severely effected patients. Baclofen is a zwitterionic, hydrophilic molecule that does not readily penetrate the blood-brain barrier. The enhanced efficacy and reduced side effects associated with baclofen delivered intrathecally provides higher concentrations of baclofen in CSF than baclofen delivered orally. For example, pharmacokinetic data shows that baclofen levels in the cisternal CSF, at the base of the brain, after lumbar intrathecal administration are approximately 20–30 times higher in the CSF than levels after oral administration to treat spasticity. Knutsson, E., U. Lindblom, et al. (1974). "Plasma and cerebrospinal fluid levels of baclofen (Lioresal) at optimal therapeutic responses in spastic paresis." *Journal of the neurological Sciences* 23: 473–484. Kroin, J. S. (1992). "Intrathecal drug administration." *Clin Pharmacokinet* 22(5): 319–326. Kroin, J. S. and R. D. Penn (1991). Cerebrospinal fluid pharmacokinetics of lumbar intrathecal baclofen. *Parenteral drug therapy in spasticity and parkinson's disease*. L. e. al. Carnforth, Parthenon Publishing: 67–77. Muller, H., J. Zierski, et al. (1988). Pharmacokinetics of intrathecal baclofen. *Local-spinal therapy of spasticity*. Z. J. Muller H, Penn R D. Berlin, Springer-Verlag: 223–226.

Baclofen may be delivered in a range of concentrations between 10 and 4000 mcg/ml. In one embodiment, baclofen may be delivered at a concentration between 1000 and 4000 mcg/ml. In another embodiment, baclofen may be delivered at a concentration between 20 and 200 mcg/ml. The higher concentration reduces the amount of time between pump reservoir refills whereas the lower concentrations may allow for a greater amount of volume to be delivered intrathecally. In addition, the daily dosage of baclofen to be administered may depend upon the particular treatment protocol to be administered. For example, in one treatment protocol the daily dosage of baclofen administered may range between 20 and 2000 mcg/day. Whereas, in different treatment protocols, the daily dosage of baclofen administered may range between 50 and 2000 mcg/day or between 1000 and 4000 mcg/day.

Another GABA agonist muscimol may also be intrathecally delivered into the CSF as a therapeutic agent alone or in combination with other therapeutic agents in an attempt to decrease the aberrant neural activity associated with tinnitus. Unlike baclofen, which is a selective $GABA_B$ agonist, muscimol is a selective $GABA_A$ agonist that inhibits neuronal activity by activating chloride channels leading to neuronal hyperpolarization.

In addition, a $GABA_A$ agonist family of therapeutics, benzodiazepines, may also be intrathecally delivered into the CSF as a therapeutic agent alone or in combination with other therapeutic agents. The benzodiazepines may be comprised of the therapeutics midazolam or alprazolam.

A GABA-agonist-like drug, gabapentin, may also be administered intrathecally in the treatment of tinnitus. Gabapentin may be delivered in a range of concentrations between 0.1 and 100 mg/ml. In one embodiment, gabapentin may be delivered at a concentration between 1 and 90 mg/ml. In another embodiment, baclofen may be delivered at a concentration between 1 and 80 mg/ml. In addition, the daily dosage of gabapentin to be administered may depend upon the particular treatment protocol. For example, in one treatment protocol the daily dosage of baclofen administered may range between 1 and 150 mg/day. Whereas, in different treatment protocols, the daily dosage of baclofen administered may range between 1 and 150 mg/day or between 2 and 60 mg/day.

Similarly, local anesthetics such as lidocaine or bupivacaine may also be intrathecally delivered into the CSF as a therapeutic agent alone or in combination with other therapeutic agents in an attempt to decrease the aberrant neural activity associated with tinnitus.

In addition, a serotonin agonist such as sumatripatan may also be intrathecally delivered into the CSF as a therapeutic agent alone or in combination with other therapeutic agents in an attempt to decrease the aberrant neural activity associated with tinnitus.

Also, a thyrotropin-releasing hormone or a therapeutic agent such as sodium valporate may also be intrathecally delivered into the CSF alone or in combination with other therapeutic agents to treat tinnitus.

Referring to FIG. 4, an implantable medical device known as an implantable therapeutic pump 40 is implanted into a patient. The location of pump implantation is one in which the implantation interferes as little as practicable with patient activity, such as subcutaneous in the lower abdomen. The proximal end 35 of a catheter 38 is connected to the implantable therapeutic pump outlet. The catheter 38 is a flexible tube with a lumen typically running the length of the catheter 38. The distal end 33 of catheter 38 is positioned to infuse a fluid into the target area of CSF of the patient. The pumped fluid may comprise a therapeutic agent such as gabapentin, sodium valproate, or a thyrotropin-releasing hormone. The pumped fluid may also comprise a solvent to be delivered to the patient. The solvent may comprise sterile water or a 0.9% saline solution. In addition, the pumped fluid may comprise an effective amount of NaCl to make the drug formulation isotonic.

The target area of CSF of the patient may be the subarachnoid space 3 between the fourth cervical vertebrae (C4) 52 and seventh cervical vertebrae (C7) 54, as shown in FIG. 5. In addition, other target areas of the CSF of the patient may include the subarachnoid space 3 between the fifth thoracic (T5) 49 (FIG. 4) and the first cervical vertebrae (C1) 56, or the subarachnoid space 3 between the fifth lumbar (L5) 48 (FIG. 4) and fifth thoracic vertebrae (T5) 49 (FIG. 4). The implantable therapeutic pump 40 is operated to discharge a predetermined dosage of the pumped fluid into the CSF of the patient.

The implantable therapeutic pump 40 contains a microprocessor 42 or similar device that can be programmed to control the amount of fluid delivery. The programming may be accomplished with an external programmer/control unit via telemetry. A controlled amount of fluid comprising therapeutics may be delivered over a specified time period. With the use of the implantable therapeutic pump 40, different dosage regimens may be programmed for a particular patient. Additionally, different therapeutic dosages can be programmed for different combinations of fluid comprising therapeutics. Those skilled in the art will recognize that a programmed implantable therapeutic pump 40 allows for starting conservatively with lower doses and adjusting to a more aggressive dosing scheme, if warranted, based on safety and efficacy factors.

The embodiments of the invention, and the invention itself, are now described in such full, clear, concise and exact terms to enable a person of ordinary skill in the art to make and use the invention. To particularly point out and distinctly claim the subject matters regarded as invention, the following claims conclude this specification. To the extent variations from the preferred embodiments fall within the limits of the claims, they are considered to be part of the invention, and claimed.

I claim:

1. A method of treating tinnitus, the method comprising:
   implanting a catheter having a proximal end and a distal end, the distal end adapted to infuse a drug formulation intrathecally into a patient's cerebrospinal fluid, the drug formulation comprising at least one therapeutic agent and a solvent; and
   infusing the drug formulation through the distal end of the catheter.

2. The method of claim 1, wherein the solvent comprises sterile water.

3. The method of claim 1, wherein the solvent comprises 0.9% saline solution.

4. The method of claim 1, wherein the solvent comprises an effective amount of NaCl to make the drug formulation isotonic.

5. The method of claim 1, wherein the drug formulation has a pH between 4 and 9.

6. The method of claim 1, wherein the drug formulation has a pH between 5 and 7.

7. The method of claim 1, wherein the drug formulation is substantially free of preservatives.

8. The method of claim 1, wherein the drug formulation comprises cyclodextrin.

9. The method of claim 1, wherein the at least one therapeutic agent comprises a $GABA_B$ agonist.

10. The method of claim 9, wherein the $GABA_B$ agonist comprises baclofen.

11. The method of claim 10, wherein the baclofen has a concentration between 10 and 4000 mcg/ml.

12. The method of claim 10, wherein the baclofen has a concentration between 50 and 2000 mcg/ml.

13. The method of claim 10, wherein the baclofen has a concentration between 1000 and 4000 mcg/ml.

14. The method of claim 10, wherein the infusing baclofen comprises a daily dose between 20 and 2000 mcg.

15. The method of claim 10, wherein the infusing baclofen comprises a daily dose between 50 and 1500 mcg.

16. The method of claim 10, wherein the infusing baclofen comprises a daily dose between 100 and 1000 mcg.

17. The method of claim 1, wherein the at least one therapeutic agent comprises gabapentin.

18. The method of claim 1, wherein the at least one therapeutic agent comprises a thyrotropin-releasing hormone.

19. The method of claim 1, wherein the at least one therapeutic agent comprises sodium valproate.

20. The method of claim 1, wherein the at least one therapeutic agent comprises a $GABA_A$ agonist.

21. The method of claim 1, wherein the $GABA_A$ agonist comprises benzodiazepine.

22. The method of claim 21, wherein benzodiazepine comprises midazolam.

23. The method of claim 21, wherein benzodiazepine comprises alprazolam.

24. The method of claim 1, wherein the distal end of the catheter is placed in subarachnoid space between fifth thoracic and first cervical vertebrae.

25. The method of claim 1, wherein the distal end of the catheter is placed in subarachnoid space between fifth lumbar and fifth thoracic vertebrae.

26. A method of treating tinnitus using gabapentin, the method comprising:
    implanting a catheter having a proximal end coupled to a pump and a distal end inserted into the subarachnoid space of a patients spinal column; and
    operating the pump to deliver a fluid comprising gabapentin directly into the cerebrospinal fluid contained in the subarachnoid space of the patient's spinal column.

27. The method of claim 26, wherein the pumped fluid has a gabapentin concentration between 0.1 and 100 mg/ml.

28. The method of claim 26, wherein the pumped fluid has a gabapentin concentration between 1 and 90 mg/ml.

29. The method of claim 26, wherein the pumped fluid has a gabapentin concentration between 1 and 80 mg/ml.

30. The method of claim 26, wherein the gabapentin delivered comprises a daily dose between 1 and 200 mg.

31. The method of claim 26, wherein the gabapentin delivered comprises a daily dose between 1 and 150 mg.

32. The method of claim 26, wherein the gabapentin delivered comprises a daily dose between 2 and 60 mg.

33. The method of claim 26, wherein the distal end of the catheter is placed in the subarachnoid space between fifth thoracic and first cervical vertebrae.

34. The method of claim 26, wherein the distal end of the catheter is placed in the subarachnoid space between fifth lumbar and fifth thoracic vertebrae.

35. The method of claim 26, wherein the pumped fluid also comprises a solvent.

36. The method of claim 35, wherein the solvent comprises sterile water.

37. The method of claim 35, wherein the solvent comprises 0.9% saline solution.

38. The method of claim 35, wherein the solvent comprises an effective amount of NaCl to make the drug formulation isotonic.

39. A method of treating tinnitus using a thyrotropin-releasing hormone, the method comprising:
    implanting a catheter having a proximal end coupled to a pump and a distal end inserted into the subarachnoid space of a patients spinal column; and
    operating the pump to deliver a fluid comprising the thyrotropin-releasing hormone directly into the cerebrospinal fluid contained in the subarachnoid space of the patient's spinal column.

40. The method of claim 39, wherein the distal end of the catheter is placed in the subarachnoid space between fifth thoracic and first cervical vertebrae.

41. The method of claim 39, wherein the distal end of the catheter is placed in the subarachnoid space between fifth lumbar and fifth thoracic vertebrae.

42. The method of claim 39, wherein the pumped fluid also comprises a solvent.

43. The method of claim 42, wherein the solvent comprises sterile water.

44. The method of claim 42, wherein the solvent comprises 0.9% saline solution.

45. The method of claim 42, wherein the solvent comprises an effective amount of NaCl to make the drug formulation isotonic.

46. A method of treating tinnitus using sodium valproate, the method comprising:
    implanting a catheter having a proximal end coupled to a pump and a distal end inserted into the subarachnoid space of a patients spinal column; and
    operating the pump to deliver a fluid comprising sodium valproate directly into the cerebrospinal fluid contained in the subarachnoid space of the patient's spinal column.

47. The method of claim 46, wherein the distal end of the catheter is placed in the subarachnoid space between fifth thoracic and first cervical vertebrae.

48. The method of claim 46, wherein the distal end of the catheter is placed in the subarachnoid space between fifth lumbar and fifth thoracic vertebrae.

49. The method of claim 46, wherein the pumped fluid also comprises a solvent.

50. The method of claim 49, wherein the solvent comprises sterile water.

51. The method of claim 49, wherein the solvent comprises 0.9% saline solution.

52. The method of claim 49, wherein the solvent comprises an effective amount of NaCl to make the drug formulation isotonic.

53. Method for treating tinnitus, the method comprising of:
    intrathecally administering drug formulation comprising at least one therapeutic agent and a solvent in an amount effective to treat tinnitus.

54. The method of claim 53, wherein the at least one therapeutic agent comprises baclofen.

55. The method of claim 53, where in the at least one therapeutic agent comprises gabapentin.

* * * * *